United States Patent [19]

Hu et al.

[11] Patent Number: 5,922,897
[45] Date of Patent: Jul. 13, 1999

[54] SURFACTANT PROCESSES

[75] Inventors: Nan-Xing Hu, Oakville; H. Bruce Goodbrand, Hamilton, both of Canada

[73] Assignee: Xerox Corporation, Stamford, Conn.

[21] Appl. No.: 09/086,856

[22] Filed: May 29, 1998

[51] Int. Cl.$^6$ ....................................................... C07F 9/09
[52] U.S. Cl. ............................ 558/122; 558/165; 558/186
[58] Field of Search ..................................... 558/122, 165, 558/186

[56] References Cited

U.S. PATENT DOCUMENTS

| | | | |
|---|---|---|---|
| 3,799,956 | 3/1974 | Nakamura et al. | 558/186 |
| 3,819,750 | 6/1974 | Shim | 558/165 |
| 4,072,704 | 2/1978 | Langdon | 260/463 |
| 4,353,834 | 10/1982 | Langdon | 260/404.5 |
| 4,385,000 | 5/1983 | Walz et al. | 558/186 X |
| 4,983,488 | 1/1991 | Tan et al. | 430/137 |
| 4,996,127 | 2/1991 | Haswgawa et al. | 430/109 |
| 5,278,020 | 1/1994 | Grushkin et al. | 430/137 |
| 5,290,654 | 3/1994 | Sacripante et al. | 430/137 |
| 5,308,734 | 5/1994 | Sacripante et al. | 430/137 |
| 5,344,738 | 9/1994 | Kmiecik-Lawrynowicz et al. | 430/137 |
| 5,346,797 | 9/1994 | Kmiecik-Lawrynowicz et al. | 430/137 |
| 5,348,832 | 9/1994 | Sacripante et al. | 430/109 |
| 5,364,729 | 11/1994 | Kmiecik-Lawrynowicz et al. | 430/137 |
| 5,366,841 | 11/1994 | Patel et al. | 430/137 |
| 5,370,963 | 12/1994 | Patel et al. | 430/137 |
| 5,403,693 | 4/1995 | Patel et al. | 430/137 |
| 5,405,728 | 4/1995 | Hopper et al. | 430/137 |
| 5,418,108 | 5/1995 | Kmiecik-Lawrynowicz et al. | 430/137 |
| 5,496,676 | 3/1996 | Croucher et al. | 430/137 |
| 5,501,935 | 3/1996 | Patel et al. | 430/137 |
| 5,527,658 | 6/1996 | Hopper et al. | 430/137 |
| 5,585,215 | 12/1996 | Ong et al. | 430/137 |
| 5,650,255 | 7/1997 | Ng et al. | 430/137 |
| 5,650,256 | 7/1997 | Veregin et al. | 430/137 |

*Primary Examiner*—Michael G. Ambrose
*Attorney, Agent, or Firm*—E. O. Palazzo

[57] ABSTRACT

A process for the preparation of surfactants is described comprising reacting a phosphorus acid ester of the following Formula (IV)

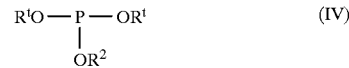

wherein $R^t$ is aryl, $R^2$ is alkyl or aryl, with a hydrophilic polyoxyalkylene of the following Formulas (VIII), or (IX)

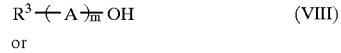

or
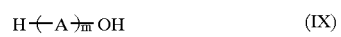

wherein $R^3$ is alkyl and A is a hydrophilic polyoxyalkylene chain, and which reaction results in an intermediate compound Formulas (XI), (XII), or (XIII);

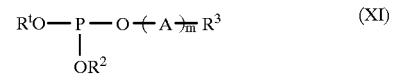
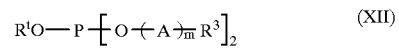
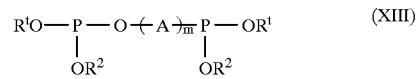

reacting the intermediate compound selected from the group consisting of Formulas (XI) through (XIII), with a hydroxylic compound $R^1$-OH (X) to yield surfactant precursors comprised of Formulas (V), (VI), and (VII), respectively:

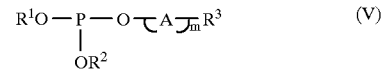
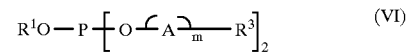
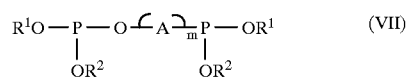

and, oxidizing said phosphorus ester-linked surfactant precursors selected from the group consisting of Formulas (V), (VI) and (VII), with an oxidizing agent to produce the surfactants.

25 Claims, No Drawings

SURFACTANT PROCESSES

PENDING APPLICATIONS

There are illustrated in copending applications U.S. Ser. No. 960,176, the disclosure of which is totally incorporated herein by reference, toner processes wherein cleavable surfactants of Formulas (I), (II), (III), or mixtures thereof can be selected and wherein processes for the preparation of of these surfactants are disclosed, and in U.S. Ser. No. 960,754, the disclosure of which is totally incorporated herein by reference, there are illustrated surfactant processes. The present invention relates to improved, and one step processes for the preparation of the surfactants of the above copending applications.

The nonionic surfactant compositions of the above copending applications can be formed by the stepwise esterification of a phosphorus oxyhalide with hydroxylic components (a component containing a hydroxy group) as illustrated in the following reaction scheme.

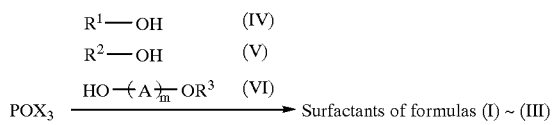

wherein X is a halide, such as chloride or bromide, $R^1$ is an alkyl of, for example, from about 4 to about 60 carbon atoms, or an aryl group having from about 6 to about 60 carbon atoms; $R^2$ may be the same as $R^1$ or different, and can be selected from the group consisting of alkyl of 1 to about 60 carbon atoms, and aryl having from about 6 to about 60 carbon atoms; $R^3$ is hydrogen or alkyl of from, for example, about 1 to 10, and preferably 1 to 3 carbon atoms; A is a hydrophilic polymer chain selected from the group consisting of polyoxyalkylene, poly(vinyl alcohols), poly (saccharides) and the like, and preferably is a polyoxyalkylene.

The present invention process relates to the preparation of nonionic surfactants comprised, for example, of the stepwise transesterification of a phosphorus triester with corresponding hydroxylic components, followed by oxidation with, for example, a peroxide as illustrated in the following Scheme.

wherein $R^1$ is a transferring group, such as aryl, containing, for example, from about 6 to about 10 carbon atoms; $R^1$, $R^2$, $R^3$ and A are as illustrated in the copending applications. The invention process provides a number of advantages with respect to the processes of the copending applications, such as the elimination of corrosive chemicals, such as phosphorus oxychloride, and the avoidance of the generation of hydrogen chloride, thus the invention processes are, for example, environmentally acceptable.

BACKGROUND OF THE INVENTION

The present invention is generally directed to surfactants, and more specifically, to processes for the preparation of nonionic surfactant compositions comprising a hydrophobic group and a hydrophilic group linked by a phosphate ester, and which nonionic surfactant compositions can be cleaved or converted into a substantially inert form by exposure to, for example, basic mediums, or basic solutions, and wherein the pH thereof is, for example, from about 8 to about 13, and preferably from about 8 to about 12. The nonionic surfactant compositions can be utilized for the preparation of toners by emulsion/aggregation/coalescence processes as illustrated in U.S. Ser. Nos. 960,176 and 960,754; U.S. Pat. No. 5,290,654, U.S. Pat. No. 5,278,020, U.S. Pat. No. 5,308,734, U.S. Pat. No. 5,370,963, U.S. Pat. No. 5,344,738, U.S. Pat. No. 5,403,693, U.S. Pat. No. 5,418,108, U.S. Pat. No. 5,364,729, and U.S. Pat. No. 5,346,797; and also U.S. Pat. Nos. 5,348,832; 5,405,728; 5,366,841; 5,496,676; 5,527,658; 5,585,215; 5,650,255; 5,650,256 and 5,501,935 (spherical toners), the disclosures of which are totally incorporated herein by reference.

PRIOR ART

A number of surfactants, such as nonionic surfactants, and processes are known. Usually, these surfactants are stable in acid, basic and neutral media. In some applications, however, it is necessary or at least highly desirable to modify or change the surface activity of the surfactant in toner processes, and in these process situations the presence of the surfactant after its use, such as the emulsion/aggregation toner processes of the appropriate U.S. patents recited herein, can result in toner products with undesirable char- Scheme 1

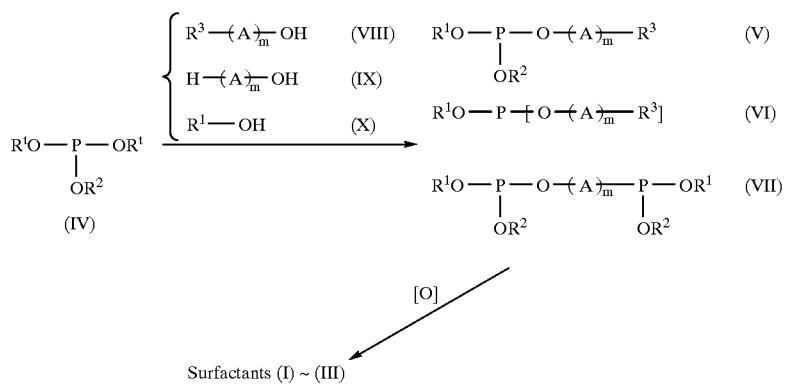

acteristics. For example, in the processes for the preparation of toners, as illustrated in U.S. Pat. Nos. 4,996,127 and 4,983,488, the disclosures of which are totally incorporated herein by reference, the nonionic surfactants are preferably removed from the toner generated primarily because their presence may significantly adversely affect the toner charging, such as triboelectric charging characteristics. To remove such surfactants, however, requires lengthy and numerous washing processes which can be costly, time-consuming, and generate large volumes of waste water. In addition, these type of nonionic surfactants are not easily biodegradable rendering such surfactants upon disposal a possible, or potential source of water pollution.

In U.S. Pat. Nos. 4,072,704 and 4,353,834, there are disclosed carbonate and carboxylic acid ester group containing nonionic surfactants. There is no indication in these patents, however, that, for example, phosphate ester linkages are present, and also, these prior art type of surfactants are not believed to be as suitable for the preparation of toners. Also, these prior art surfactants can be sensitive to acid conditions and break down, or decompose in acidic media, thus rendering them substantially ineffective for emulsion polymerizations which are generally conducted under acidic conditions. The phosphate based surfactants of the present invention are relatively stable, that is they do not substantially decompose in acidic media and therefore can be effectively utilized in emulsion polymerizations. The low stability of the phosphate based surfactants in basic media renders the latexes prepared with these surfactants ideally suited for the preparation of toners since they can be readily hydrolyzed or broken down by, for example, a base compound after toner preparation, thus enabling a chemical toner process with minimum or no post-reaction washing.

SUMMARY OF THE INVENTION

It is a feature of the present invention to provide processes for nonionic surfactant compositions with many of the advantages illustrated herein.

In another feature of the present invention there are provided processes for surfactant compositions which are cleavable by exposure to, or mixing with, for example, a basic medium, which promotes hydrolytic cleavage of the surfactant molecules, and wherein there is eliminated corrosive reactant chemicals such as phosphorus oxychloride.

Further, in a feature of the present invention there are provided processes for nonionic surfactant compositions comprised of a hydrophobic group and a hydrophilic group linked by a phosphate ester linkage.

Yet in another feature of the present invention there are provided processes for nonionic surfactant compositions comprised of phosphate ester-linked hydrophilic chains, and which chains are, for example, selected from the group consisting of polyoxyalkylene glycols and the like, and which polymers contain at least one terminal hydrophobic group comprised of, for example, alkyl, alkylaryl, arylalkyl, or alkylarylalkyl.

The present invention relates to processes for the preparation of nonionic surfactant compositions of Formulas (I), (II), or (III), or mixtures thereof.

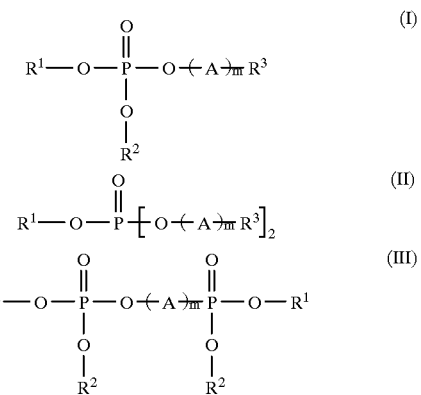

wherein $R^1$ is a hydrophobic moiety selected from, for example, the group consisting of alkyl, aryl, and their substituted derivatives, such as those derivatives containing a halogen atom such as fluorine, chlorine or bromine, and wherein the alkyl group contains, for example, from about 4 to about 60, and preferably from about 6 to about 30 carbon atoms and the aryl group contains, for example, from about 6 to about 60, and preferably from about 10 to about 30 carbon atoms; $R^2$ may be the same as $R^1$ or different, and can be selected from the group consisting of alkyl, aryl, and their substituted derivatives such as halogenated alkyl or halogenated aryl; $R^3$ is hydrogen or alkyl of from, for example, about 1 to about 10, and preferably 1 to 3 carbon atoms; A is a hydrophilic polymer chain selected, for example, from the group consisting of polyoxyalkylenes, and preferably is a polyoxyalkylene derived from the same or different alkylene oxides with from about 2 to about 4 carbon atoms, and more specifically, A is a polyoxyethylene glycol or a poly (ethylene glycol) with an average molecular weight $M_W$ of from about 104 to about 2,500; and m is the number of repeating units of the hydrophilic polymer chain, and can be a number of, for example, from about 2 to about 500, and preferably from about 5 to about 100, and which processes comprise the successive transesterifications of a phosphorus acid ester with corresponding hydroxylic components, followed by oxidation with, for example, a peroxide as illustrated in Scheme 1

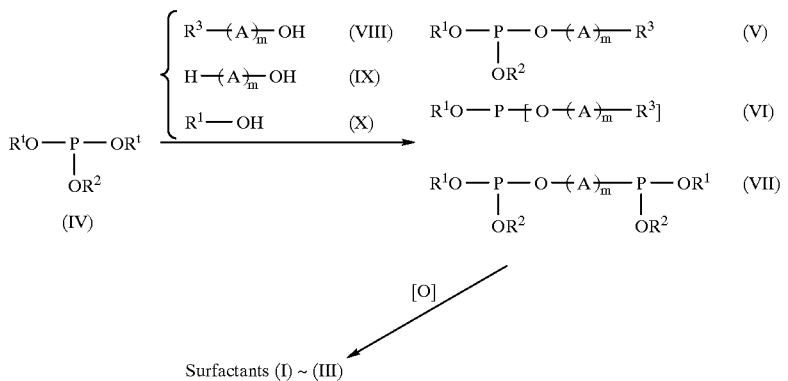

Scheme 1 wherein R' is a transferring group comprised of an aryl containing from about 6 to about 10 carbon atoms, and $R^1$, $R^2$, $R^3$ and A are as illustrated herein. The intermediates formed may be isolated, or are preferably selected for the oxidation reaction without isolation.

The nonionic surfactant compositions of Formulas (I), (II), (III), or mixtures thereof, wherein the total of components in the mixture is equal to about 100 percent, for example, a mixture comprising one main component mixed with a second component in an amount of from 1 to about 30 weight percent of the main component, wherein the main component and the second component are selected from the surfactants of Formulas (I) through (III); and which surfactants are comprised of a hydrophobic and a hydrophilic moiety linked together by a phosphate ester linkage, can be selected for toner processes. With the presence of the phosphate ester linkage, the surfactant compositions can, for example, be decomposed, or converted into nonsurface-active species or into new surface-active derivatives with different molecular properties upon exposure to conditions of, for example, basic medium which promote hydrolytic cleavage of the surfactant molecules. More specifically, the nonionic surfactant compositions illustrated herein can be selected for known emulsion/aggregation/coalescense processes for the preparation of chemical toners, and wherein the nonionic surfactant compositions can be readily decomposed by treatment with a dilute aqueous base solution into water soluble components, which components can be removed from the toner generated by a limited number of washings, thus enabling the provision of toners with excellent charging characteristics.

DESCRIPTION OF EMBODIMENTS

This invention relates to the processes for the preparation of surfactant compositions containing phosphate ester linkages as represented by Formulas (I) through (III).

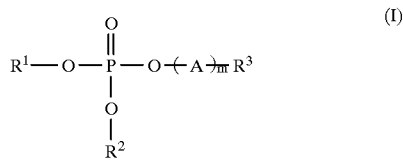

-continued $$R^1 - O - \overset{\overset{\displaystyle O}{\|}}{P} + O + A \xrightarrow{}_m R^3]_2 \qquad (II)$$

$$R^1 - O - \overset{\overset{\displaystyle O}{\|}}{\underset{\underset{\displaystyle R^2}{|}}{\underset{\displaystyle O}{|}}{P}} - O + A \xrightarrow{}_m \overset{\overset{\displaystyle O}{\|}}{\underset{\underset{\displaystyle R^2}{|}}{\underset{\displaystyle O}{|}}{P}} - O - R^1 \qquad (III)$$

wherein the Rs and A represent suitable substituents, and more specifically, wherein $R^1$ is a hydrophobic moiety, such as an aliphatic or aromatic group like alkyl or aryl; $R^2$ is selected from the group consisting of alkyl and aryl; R3 is hydrogen or alkyl; A is a hydrophilic polymer chain; and m is the number of repeating segments of the hydrophilic polymer chain A; or wherein the surfactant $R^1$ alkyl contains from about 4 to about 60 carbon atoms, $R^1$ aryl contains from about 6 to about 60 carbon atoms; $R^2$ alkyl contains from 1 to about 60 carbon atoms, $R^2$ aryl contains from about 6 to about 60 carbon atoms; $R^3$ alkyl contains from 1 to about 10 carbon atoms; and m is a number of from about 2 to about 500; wherein A is selected from the group consisting of polyoxyalkylene, wherein each hydrophilic polymer can be formed as block, branched, copolymeric, or homopolymeric polymers; wherein A is a hydrophilic polyoxyalkylene chain derived from the same or different alkylene oxides with from about 2 to about 4 carbon atoms; wherein $R^1$ is an alkylaryl, and wherein alkyl contains from about 4 to about 30 carbon atoms and aryl contains from about 6 to about 10 carbon atoms; $R^2$ is an alkyl containing from 1 to about 30 carbon atoms or an aryl containing from about 6 to about 10 carbon atoms; $R^3$ is hydrogen or alkyl of from 1 to about 5 carbon atoms; and wherein A is a hydrophilic polymer chain with the number of repeating segments m being from about 5 to about 100; wherein said alkylaryl is an alkylphenyl, wherein $R^2$ is an alkyl group; a surfactant composition wherein said alkyl group contains 1 to about 6 carbon atoms; wherein alkyl group is methyl; wherein $R^2$ is an aryl group that contains from about 6 to about 30 carbon atoms; wherein that aryl group is a phenyl; wherein $R^3$ is hydrogen or methyl; wherein A is a poly (ethylene glycol) chain with the number of repeating units m being from about 5 to about 100; wherein $^1$ or $R^2$ contains a substituent selected from the group consisting of fluorine, chlorine, and bromine; wherein $R^1$ is an alkylphenyl group wherein alkyl contains from about 4 to about 30 carbon atoms, $R^2$ is an alkyl group with 1 to about 6 carbon atoms, and $R^3$ is hydrogen or methyl, and wherein A is a poly (ethylene glycol) chain with the number of repeating units m being from about 5 to about 100.

In accordance with this invention, the processes comprise the successive transesterification of a phosphorus acid ester of, for example, triphenyl phosphite with corresponding hydroxylic components to generate intermediate surfactants linked with phosphorus ester linkages, followed by oxidizing the resulting phosphorus ester linkages into corresponding phosphate linkages, thus yielding the surfactants of Formulas (I) through (III) as illustrated in Scheme 1.

More specifically, the processes of the present invention comprise:

(a) reacting a phosphorus acid ester of formula

   (IV)

wherein $R^t$ is a transferring group, such as aryl, containing, for example, from about 6 to about 10 carbon atoms, $R^2$ is alkyl containing, for example, from 1 to about 60 carbon atoms, or aryl containing, for example, from about 6 to about 60 carbon atoms with a hydrophilic polyoxyalkylene of formula

   (VIII)

or

   (IX)

wherein $R^3$ is an alkyl group containing from 1 to 3 carbon atoms, A is a hydrophilic polyoxyalkylene chain of from about 5 to about 100 repeating segments;

to yield an intermediate compound comprised of Formulas (XI), (XII), or (XIII), and more specifically, wherein component (XI) results from the reaction of phosphorus ester (IV) with polyoxyalkylene (VIII); component (XII) results from the reaction of phosphorus ester (IV) with two molecules of polyoxyalkylene (VIII), and component (XIII) results from the reactions of two molecules of phosphorus ester component (IV) with polyoxyalkylene glycol (IX)

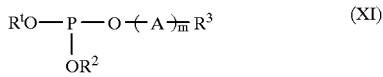   (XI)

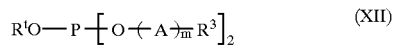   (XII)

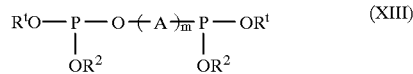   (XIII)

wherein $R^t$, $R^2$, $R^3$, and A are as indicated with respect to Formulas (I), (II), and (III);

(b) reacting successively the intermediate compound selected from the group consisting of Formulas (XI) through (XIII), with a hydroxylic compound, $R^1$-OH (X), wherein $R^1$ is an alkyl containing, for example, from about 4 to about 60 carbon atoms, or an aryl which contains, for example, from about 6 to about 60 carbon atoms to yield surfactant precursors comprised of Formulas (V), (VI), and (VII), respectively, and specifically wherein components (V) results from the reaction of component (XI) with $R^1$-OH (X); component (VI) results from the reaction of component, (XII) with $R^1$-OH (X), and component (VII) results from the reaction of component (XIII) with two parts of $R^1$-OH (X)

   (V)

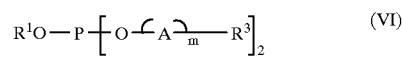   (VI)

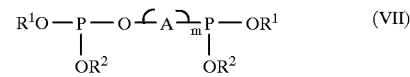   (VII)

wherein $R^1$, $R^2$, $R^3$, and A are as illustrated hereinbefore; and (c) oxidizing the resulting phosphorus ester-linked surfactant precursors selected from the group consisting of Formulas (V), (VI) and (VII) with an oxidizing agent to produce the surfactant composition of Formulas (I), (II) or (III), wherein the surfactant (I) results from the oxidation of component (V), surfactant (II) results from the oxidation of component (VI), and surfactant (III) results from the oxidation of component (VII).

The processes for the formation of the surfactant compositions of Formula (I) include the selection of from about 1 to about 1.5 molar equivalent of a phosphorus ester (IV), about 1.0 molar equivalent of a polyoxyalkylene (VIII), and from about 1.0 to about 1.5 molar equivalents of a hydroxylic compound (X). A process for the formation of surfactant compositions of Formula (II) include, for example, the reaction of from 1 to about 1.5 molar equivalent of a phosphorus ester (IV), and about 2.0 molar equivalents of a polyoxyalkylene (VIII); and a process for the formation of surfactant compositions of Formula (III) include the reactants comprised of from about 2 to about 2.5 molar equivalents of a phosphorus ester (IV), about 1.0 molar equivalent of a polyoxyalkylene (VIII), and from about 2.0 to about 2.5 molar equivalents of a hydroxylic compound (X). The transesterification reactions comprised of (a) and (b) may be performed with the sequential addition of the corresponding hydroxylic components to the phosphorus ester compound (IV) or by admixing the phosphorus ester (IV) with the hydroxylic components simultaneously. The condensation reactions are, for example, accomplished by heating at a temperature ranging from about 100° C. to about 250° C., and preferably from about 150° C. to about 230° C. under a reduced pressure ranging from about 1 millibar to about 100 millibars so that the byproduct alcohol ($R^t$OH) can be distilled off from the reaction mixture. Preferably, the reactants for the condensation described herein further include a catalyst in the amount of, for example, from about 0.005 to about 0.1 equivalent relative to the phosphorus ester (IV). Any catalysts which can promote the transesterification of phosphorus esters may be utilized in the processes of this invention. Useful examples of catalysts include metal salts, such as magnesium chloride, magnesium sulfate, potassium chloride and the like; alkaline metal hydroxides, such as sodium hydroxide, potassium hydroxide; alkaline metal alkoxides, such as sodium methoxide, sodium ethoxide, potassium tert-butoxide and the like; inorganic acids, such as hydrogen chloride, sulfuric acid and the like; and preferably the catalyst is a metal salt like magnesium chloride.

The phosphorus triester (IV) employed herein preferably comprises an $R^t$ radical of a phenyl group or its derivatives, such as tolyl, fluorophenyl, chlorophenyl and the like, from which the byproduct R'OH can be easily removed. Useful examples of phosphorus triester (IV) are triphenyl phosphite, diphenylmethyl phosphite, tri-tolyl phosphite, p-tert-octylphenyl diphenyl phosphite, dodecyl diphenyl phosphite and the like, and preferably triphenyl phosphite.

The hydrophilic polymers of Formulas (VIII) or (IX) can be selected, for example, from the group consisting of block, branched, copolymeric, or homopolymeric polyoxyalkylenes having at least one terminal hydroxyl group. Specific examples of polyoxyalkylenes are those polymerized from the same or different alkylene oxides with 2 to about 4 carbon atoms, such as poly(ethylene glycol), poly(ethylene glycol) monomethyl ether, poly(propylene glycol), poly(propylene glycol) monomethyl ether, poly(ethylene oxide-propylene oxide), poly(ethylene glycol)-b-poly(propylene glycol) and the like, which polymers may have a number of repeating units m of, for example, from about 2 to about 500, and preferably from about 5 to about 100. Preferred examples of hydrophilic polymers are poly(ethylene glycols) and their monomethyl ethers with the number of repeating segments selected being from about 5 to about 50.

The hydroxylic reagent of Formula (X) may be selected from aliphatic alcohols with from, for example, about 4 to about 60, and preferably from about 6 to about 30 carbon atoms. Examples of aliphatic alcohols include butanol, propanol, octanol, decanol, dodecanol, tridecanol, hexadecanol and the like, and which aliphatic alcohols may further contain a halogen atom such as fluorine, chlorine or bromine. Preferably the hydroxylic reagent of Formula (X) is comprised of aromatic alcohols, and more specifically, alkylphenols wherein alkyl may contain from about 4 to about 60 carbon atoms, and preferably from about 6 to about 30 carbon atoms, which aromatic alcohols or alkylphenols may further include a halogen atom such as fluorine, chlorine or bromine. Suitable examples of alkylphenols include octylphenol, tert-octylphenol, nonylphenol, decylphenol, dodecylphenol, hexadecylphenol, tert-octylifluorophenol, dodecylfluorophenol, fluorododecylphenol and the like.

The processes of the present invention comprise an oxidation reaction (c) which converts the surfactant precursors of Formulas (V) through (VII) into the intended surfactant compositions of Formulas (I) through (III), wherein the oxidation of component (V) results in surfactant (I), the oxidation of component (VI) results in surfactant (II), and the oxidation of component (VII) results surfactant (III). This oxidation may be effected at about 0° C. to about 50° C., or from about 20° C. to about 35° C. in an inert solvent such as toluene, ethyl acetate, dichloromethane, and the like. Preferably from about 1.0 to about 2.0 equivalents of an oxidizing agent are used, and which agents can convert the phosphorus triesters into phosphate esters. Examples of oxidizing agents include hydrogen peroxide, ozone, alkyl peroxides wherein alkyl may contain from about 1 to about 10 carbon atoms, such as tert-butyl hydroperoxide, cumenyl hydroperoxide and the like, peroxyacides, such as performic acid, peracetic acid, perbenzoic acid and the like, and preferably hydrogen peroxide. The oxidation may also be accomplished with an oxidizing agent comprised of halogen compounds like bromine or iodine, followed by hydrolysis in water.

Also, processes of the present invention comprise the transesterification reactions of a phosphorus ester (IV) with a hydrophilic polyoxyalkylene of Formula (VIII) or (IX), and with a hydrophobic hydroxylic component R¹OH, wherein the phosphorus ester R' is selected from the group consisting of phenyl, tolyl, fluorophenyl, chlorophenyl and the like, and R² is an alkyl containing from about 1 to about 30 carbon atoms or an aryl group containing from about 6 to about 30 carbon atoms, and preferably R² is a phenyl group, the polyoxyalkylene is comprised of poly(ethylene glycols) or its monoalkyl ethers having R³ of from 1 to about 3 carbon atoms, and said hydroxylic component R¹OH is comprised of alkylphenols wherein said alkyl contains from about 6 to about 30 carbon atoms, and which transesterification reactions are accomplished by heating the reactants at, for example, from about 150° C. to about 230° C. under a reduced pressure of, for example, about 1 millibar to about 100 millibars in the presence of a catalyst of, for example, magnesium chloride, and followed by treatment of the resulting surfactant precursor compositions with an oxidizing agent of, for example, hydrogen peroxide.

The processes of the present invention can be selected for the synthesis of the nonionic surfactant compositions of Formulas (I), (II), (III), or mixtures thereof, wherein the total of components in the mixture is equal to about 100 percent, and which surfactants can be selected for toner processes. Illustrative examples of components generated are poly(ethylene glycol)-α-methyl ether-ω-p-tert-octyldiphenyl phosphate, poly(ethylene glycol)-α-methyl ether-ω-octyldiphenyl phosphate, poly(ethylene glycol)-α-methyl ether-ω-decyldiphenyl phosphate, poly(ethylene glycol)-α-methyl ether-ω-dodecyldiphenyl phosphate, poly(ethylene glycol)-α-methyl ether-ω-hexadecyldiphenyl phosphate, poly(ethylene glycol)-α-methyl ether-ω-methyl p-tert-octylphenyl phosphate, bis-ω-p-tert-octylphenyl phosphate, poly(ethylene glycol)-α,ω-methyl p-tert-octylphenyl phosphate, poly(ethylene glycol) ethyl p-tert-octylphenyl phosphate, poly(ethylene glycol)-α-methyl ether-ω-ethyl p-tert-octylphenyl phosphate, poly(ethylene glycol)-α-methyl ether-ω-p-tert-octylphenyl tolyl phosphate, poly(ethylene oxide-co-propylene oxide)-α-methyl ether-ω-p-tert-octyldiphenyl phosphate, and the like, wherein the polymer chains contain, for example, from about 5 to about 50 repeating units or segments.

Aspects of the present invention are a process for the preparation of a surfactant represented by Formulas (I), (II) or (III); or optionally mixtures thereof

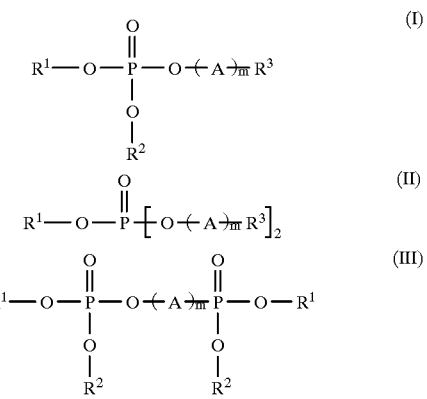

wherein R¹ is a hydrophobic moiety preferably of, for example, alkyl or aryl; R² is preferably selected from the group consisting of alkyl and aryl; R³ is preferably hydrogen or alkyl; A is a hydrophilic polymer chain; and m is the number of repeating segments of the hydrophilic polymer chain A; and which process comprises:

(a) reacting a phosphorus acid ester of the following Formula (IV)

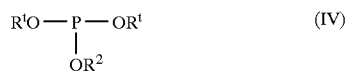

wherein $R^1$ is aryl, $R^2$ is alkyl or aryl with a hydrophilic polyoxyalkylene of the following Formulas (VIII), or (IX)

$$R^3\text{---}(A)_{\overline{m}}\text{OH} \quad (VIII)$$

or $$H\text{---}(A)_{\overline{m}}\text{OH} \quad (IX)$$

wherein $R^3$ is alkyl with, for example, from about 1 to about 6 carbon atoms, and A is a hydrophilic polyoxyalkylene chain, and which reaction results in an intermediate compound Formulas (XI), (XII), or (XIII), wherein component (XI) results from the reaction of phosphorus ester (IV) with polyoxyalkylene (VIII); component (XII) results from the reaction of phosphorus ester (IV) with polyoxyalkylene (VIII), and component (XIII) results from the reactions of phosphorus ester component (IV) with polyoxyalkylene glycol (IX)

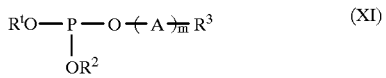

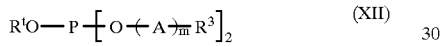

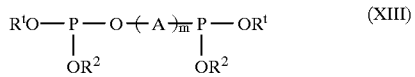

(b) reacting the intermediate compound selected from the group consisting of Formulas (XI) through (XIII), with a hydroxylic compound, $R^1$-OH (X), to yield surfactant precursors comprised of Formulas (V), (VI), and (VII) respectively, wherein component (V) results from the reaction of component (XI) with $R^1$-OH (X); component (VI) results from the reaction of component (XII) with $R^1$-OH (X), and component (VII) results from the reaction of component (XIII) with $R^1$-OH (X), wherein $R^1$ is as illustrated herein, and is, for example, an aliphatic like alkyl, or an aromatic like aryl group

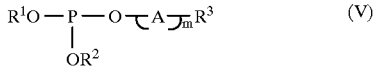

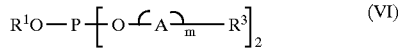

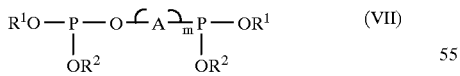

(c) oxidizing said phosphorus ester-linked surfactant precursors (b) selected from the group consisting of Formulas (V), (VI) and (VII), with an oxidizing agent to produce the surfactant composition of Formulas (I), (II) or (III), wherein the surfactant (I) results from the oxidation of component (V), surfactant (II) results from the oxidation of component (VI), and surfactant (III) results from the oxidation of component (VII); a process wherein there is accomplished a transesterification reaction of (a) and (b), and which reaction is effected by heating at a temperature of about 150° C. to about 250° C. under a reduced pressure of from about 1.0 to about 100 bar, and wherein the byproduct of $R'$OH is optionally removed; a process wherein the reactants for the formation of surfactant compositions of Formula (I) comprise from 1 to about 1.2 molar equivalents of a phosphorus ester (IV), about 1.0 molar equivalent of a polyoxyalkylene (VIII), and from about 1.0 to about 1.2 molar equivalents of (X); a process wherein the reactants for the formation of surfactant compositions of Formula (II) comprise from 1 to about 1.2 molar equivalent of a phosphorus ester (IV), and about 2.0 molar equivalents of a polyoxyalkylene (VIII); a process wherein the reactants for the formation of surfactant compositions of Formula (III) comprise from 2 to about 2.4 molar equivalents of a phosphorus ester (IV), about 1.0 molar equivalent of a polyoxyalkylene (VIII), and from about 2.0 to about 2.4 molar equivalents of an alcoholic compound (X); a process wherein there is accomplished a transesterification reaction of (a) and (b), and which reaction further includes a catalyst in the amounts ranging from about 0.001 to about 0.1 equivalent based on the starting phosphorus ester (IV), and which catalyst is selected from the group consisting of metal salts, alkaline metal hydroxides, and alkaline metal alkoxides; a process wherein said metal catalyst is magnesium chloride; a process wherein the oxidation (c) is accomplished in an inert solvent at from 0° C. to about 60° C. with an oxidizing agent selected from the group consisting of hydrogen peroxide, ozone, organic hydrogen peroxides, and peracids; process wherein said oxidizing agent is hydrogen peroxide or tert-butyl hydrogen peroxide; a process wherein said inert solvent is ethyl acetate, toluene, or dichloromethane; a process wherein said $R'$ of the phosphorus ester of Formula (IV) is selected from the group consisting of phenyl, tolyl, fluorophenyl, and chlorophenyl; a process wherein $R'$ is a phenyl; a process wherein $R^1$ alkyl contains from about 4 to about 60 carbon atoms, $R^1$ aryl contains from about 6 to about 60 carbon atoms; $R^2$ alkyl contains from about 1 to about 60 carbon atoms, $R^2$ aryl contains from about 6 to about 60 carbon atoms; $R^3$ alkyl contains from 1 to about 6 carbon atoms; and m is a number of from about 2 to about 500; a process wherein A is a hydrophilic polyoxyalkylene chain derived from the same or different alkylene oxides with from about 2 to about 4 carbon atoms; a process wherein $R^1$ is an alkylaryl, and wherein alkyl contains from about 4 to about 30 carbon atoms and aryl contains from about 6 to about 10 carbon atoms; $R^2$ is an alkyl containing from 1 to about 30 carbon atoms or an aryl containing from about 6 to about 10 carbon atoms; $R^3$ is hydrogen or alkyl of from 1 to about 3 carbon atoms; and wherein A is a hydrophilic polyoxyalkylene chain with the number of repeating segments m being from about 5 to about 100; a process wherein A is a poly(ethylene glycol) chain with the number of repeating units m being from about 5 to about 100; a process wherein $R^1$ is an alkylphenyl group wherein alkyl contains from about 4 to about 30 carbon atoms, $R^2$ is a phenyl, and $R^3$ is a methyl, and wherein A is a poly(ethylene glycol) chain with the number of repeating units m being from about 5 to about 100; a process wherein said surfactant resulting is selected from the group consisting of poly(ethylene glycol)-αmethyl ether-ω-p-tert-octyldiphenyl phosphate, poly(ethylene glycol)-αmethyl ether-ω-octyldiphenyl phosphate, poly(ethylene glycol)-α-methyl ether-ω-decyldiphenyl phosphate, poly(ethylene glycol)-α-methyl ether-ωdodecyldiphenyl phosphate, poly(ethylene glycol)-α-methyl ether-ωhexadecyldiphenyl phosphate, poly (ethylene glycol)-α-methyl ether-ωmethyl p-tert-octylphenyl phosphate, bis ω-p-tert-octylphenyl phosphate, poly(ethylene glycol)-α,ω-methyl p-tert-octylphenyl phosphate, poly(ethylene glycol) ethyl p-tert-octylphenyl phosphate, poly(ethylene glycol)-α-methyl ether-ω-ethyl p-tert-octylphenyl phosphate, poly(ethylene glycol)-α-methyl ether-ω-p-tert-octylphenyl tolyl phosphate, poly(ethylene oxide-co-propylene oxide)-α-methyl ether-ω-p-tert octyldiphenyl phosphate, and wherein the polymer chain contains from about 5 to about 50 repeating units or segments; a process wherein R' is phenyl, $R^1$ is 4-octylphenyl or 4-dodecylphenyl, $R^2$ is a phenyl or methyl, and $R^3$ is a methyl; a process wherein the a hydrophobic compound $R^1$-OH (X) is 4-tert- octylphenol or 4-dodecylphenol; a process wherein said phosphorus ester is triphenyl phosphite; a process wherein the oxidizing agent selected from the group consisting of hydrogen peroxide, ozone, organic hydrogen peroxides and peracids; a process wherein the oxidizing agent selected from the group consisting of tert-butyl hydrogen peroxide, cumene peroxide, peracetic acid and performic acid; a process for the preparation of the surfactant of a poly(ethylene glycol)-α-methyl ether-ω-p-tert-octyldiphenyl phosphate comprising the reaction of about 1.0 molar equivalent of poly(ethylene glycol) monomethyl ether with $M_n$ of from about 500 to about 2,000, from about 1.0 to about 1.5 molar equivalents of triphenyl phosphite, from about 1.0 to about 1.5 molar equivalents of 4-tert-octylphenol, and from about 0.01 to about 0.05 molar equivalent of magnesium chloride, with an oxidizing agent and wherein the oxidation optionally includes from about 1.0 to about 1.5 molar equivalents of hydrogen peroxide; and a process for the preparation of a surfactant represented by Formulas (I), (II) or (III); or optionally mixtures thereof

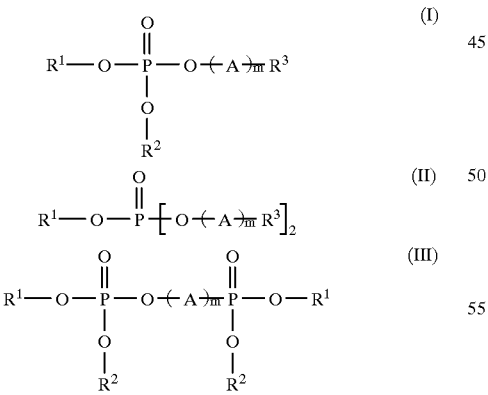

wherein $R^1$ is a hydrophobic moiety of alkyl or aryl; $R^2$ is selected from the group consisting of alkyl and aryl; $R^3$ is hydrogen or alkyl; A is a hydrophilic polymer chain; and m is the number of repeating segments of the hydrophilic polymer chain A; and which process comprises (a) reacting a phosphorus acid ester of the following Formula (IV)

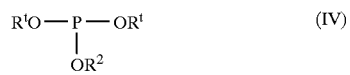

wherein R' is aryl, $R^2$ is alkyl or aryl, with a hydrophilic polyoxyalkylene of the following Formulas (VIII), or (IX)

or

wherein $R^3$ is alkyl with from about 1 to about 6 carbon atoms, and A is a hydrophilic polyoxyalkylene chain, and which reaction results in an intermediate compound Formulas (XI), (XII), or (XIII), wherein component (XI) results from the reaction of phosphorus ester (IV) with polyoxyalkylene (VIII); component (XII) results from the reaction of phosphorus ester (IV) with about two molecules of polyoxyalkylene (VIII), and component (XIII) results from the reactions of about two molecules of phosphorus ester component (IV) with polyoxyalkylene glycol (IX)

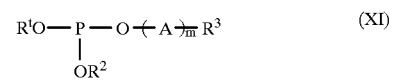

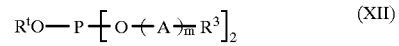

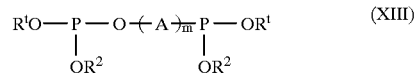

(b) reacting the intermediate compound selected from the group consisting of Formulas (XI) through (XIII) with a hydroxylic compound $R^1$-OH (X) to yield surfactant precursors comprised of Formulas (V), (VI), and (VII), respectively, wherein component (V) results from the reaction of component (XI) with $R^1$-OH (X); component (VI) results from the reaction of component (XII) with $R^1$-OH (X), and component (VII) results from the reaction of component (XIII) with about two molecules of $R^1$-OH (X)

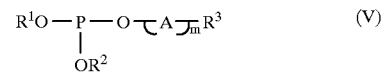

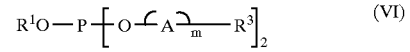

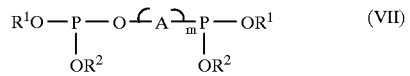

(c) oxidizing said phosphorus ester-linked surfactant precursors (B) selected from the group consisting of Formulas (V), (VI) and (VII), with an oxidizing agent to produce the surfactant composition of Formulas (I), (II) or (III), wherein the surfactant (I) results from the oxidation of component (V), surfactant (II) results from the oxidation of component (VI), and surfactant (III) results from the oxidation of component (VII).

The following Examples are provided. These Examples are intended to be illustrative only and are not intended to limit the scope of the present invention. The Example invention processes do not use corrosive chloride reagents such as phosphorus chloride and the generation of corrosive hydrogen chloride is thus avoided. A comparative Example is also provided.

EXAMPLE I

Synthesis of Poly(ethylene glycol)α-methyl Etherω-4-tert octyldiphenyl Phosphate (XIV) Wherein m is About 17;

(XIV)

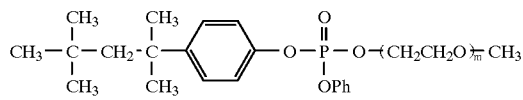

In a 3 liter round bottomed flask equipped with a mechanical stirrer and a fractionating column, a distillation head and a condenser, which was connected to a vacuum line, there were added 820 grams of poly(ethylene glycol) monomethyl ether, 420 grams of triphenyl phosphite, and 1.29 grams of magnesium chloride. The reaction mixture was then heated to about 190° C. under a vacuum of about 20 millibars, at which time phenol began to distill off. A phenol distillate in the amount of 123 grams was collected over a period of 2 hours during which time the flask contents temperature increased to about 200° C. At this point the vacuum was broken, and 279 grams of p-tert-octylphenol were added into the flask. The resulting reaction mixture was continually heated under a vacuum of 20 millibars over an additional 2.0 hours, during which time the temperature increased to 210° C. and another phenol distillate in the amount of 130 grams was collected. The resulting mixture was vacuum stripped under 5.0 millibars for 25 minutes. After cooling to room temperature (about 25° C.), the mixture was diluted with 1.0 liter of ethyl acetate and cooled with an ice bath. With stirring, 150 milliliters of 30 percent hydrogen peroxide aqueous solution were added at a rate such that the internal temperature was maintained at below 40° C. After the addition, the reaction mixture was stirred for 3.0 hours, then transferred into a separation funnel, and washed with saturated sodium chloride aqueous solution. The organic layer containing the surfactant and solvent was separated, and dried over magnesium sulfate. After the solid was filtered, the solvent in the liquid filtrate was distilled off yielding 870 grams of surfactant (XIV). The surfactant composition was characterized by proton NMR. The chemical shifts in CDCl$_3$ were 0.7 (s), 1.36 (s), 1.72 (s), 3.38 (s), 3.66 (m, PEG backbone), 4.37 (m), 7.10~7.4 (m).

COMPARATIVE EXAMPLE

In a Comparative Example, the surfactant composition of Formula (XIV) was prepared from the stepwise esterification of phosphorus oxychloride.

Preparation of 4-tert octylphenyl dichlorophosphate:

In a 500 milliliters round bottomed flask equipped with a magnetic stirrer and fitted with a reflux condenser, which was connected to a magnesium sulfate dry tube, were placed 25 grams (0.121 mole) of 4-tert-octylphenol, 57 grams (0.372 mole) of phosphorus oxychloride, and 0.35 grams (0.0036 mole) of magnesium chloride. The reaction was heated to a reflux temperature of 110° C. and maintained at this temperature for 6 hours. The unreacted phosphorus oxychloride was distilled off and the reaction mixture was cooled to room temperature, about 25° C., to provide an oily mixture which contains 39.8 grams of 4-tert-octylphenyl dichlorophosphate.

In a 1 liter round bottomed flask equipped with a magnetic stirrer, there was added the 4-tert-octylphenyl dichlorophosphate as prepared above, 11.4 grams (0.121 mol) of phenol and 500 milliliters of anhydrous toluene. Into this resulting mixture pyridine (9.6 grams, 0.121 mol) was added through the addition funnel over a period of 0.5 hour. After the addition, the reaction mixture was stirred 80° C. for an additional 3.0 hours, then cooled to about 23° C. To this mixture were added 91 grams of poly(ethylene glycol) monomethylether with an average molecular weight of 750, followed by the addition of 9.6 grams of pyridine. The resulting reaction mixture was stirred for 12.0 hours. The precipitated pyridine hydrochloride solids were filtered off and the liquid mixture was concentrated by distilling the volatile materials to yield 195 grams of a waxy solid. The surfactant composition was characterized by proton NMR. The chemical shifts in CDCl$_3$ were 0.7 (s), 1.37 (s), 1.71 (s), 3.38 (s), 3.65 (m, PEG backbone), 4.36 (m), 7.10~7.4 (m).

This process utilized a starting component of corrosive phosphorus oxychloride, which is associated with the generation of hydrogen chloride, and which hydrogen chloride was neutralized with pyridine.

EXAMPLE II

Synthesis of Poly(ethylene glycol) α-methyl Ehter ω-4-octyldiphenyl Phosphate (XIV) Wherein m is About 17:

The surfactant composition of Formula (XIV) can also be prepared in the following manner. In a 3 liter round bottomed flask equipped with a magnetic stirrer and a fractionating column, a distillation head and a condenser, which was connected to a vacuum line, there were added 150.0 grams of poly(ethylene glycol) monomethyl ether with an average molecular weight M$_W$ of 750, 75.0 grams of triphenyl phosphite, 42.0 grams of p-tert-octylphenol, and 0.6 gram of magnesium chloride. The reaction mixture was then heated to about 190° C. under a vacuum of about 20 millibars, at which time phenol began to distill off. A phenol distillate in the amount of 37.5 grams was collected over a period of 2.0 hours during which time the reaction content temperature increased to about 210° C. The resulting mixture was vacuum stripped under 5.0 millibars for 25 minutes. After cooling to room temperature (about 25° C.), the mixture resulting was diluted with 500 milliliters of ethyl acetate, and treated with 27.5 grams of 30 percent hydrogen peroxide as described in Example I producing 157.5 grams of surfactant (XIV).

EXAMPLE III

Synthesis of Poly(ethylene glycol)α-methyl Etherω-4-tert-octyldiphenyl Phosphate (XI) Wherein m is About 47:

Example I was repeated substituting a poly(ethylene glycol) monomethyl ether with an average molecular weight, M$_w$, of 2,000 for the poly(ethylene glycol) monomethyl ether of Example I. A nonionic surfactant of poly(ethylene glycol) α-methyl etherω-4-tert-octyldiphenyl phosphate (XI) with m of 47 was produced. The surfactant composition was characterized by proton NMR. The chemical shifts in CDCl$_3$ were 0.7 (s), 1.37 (s), 1.71 (s), 3.38 (s), 3.65 (m, PEG backbone), 4.37 (m), 7.10~7.40 (m).

EXAMPLE IV
Synthesis of Bisα-methyl Ether ω-methyl 4-tert-octylphenyl Phosphate (XV) Wherein m is About 17:

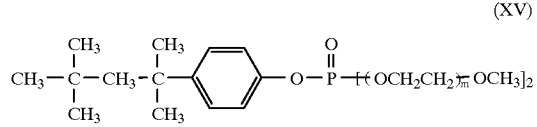 (XV)

In a 250 milliliter round bottomed flask equipped with a magnetic stirrer, a fractionating column, a distillation head and a condenser, which was connected to a vacuum line, there were added 150 grams of poly(ethylene glycol) monomethyl ether with an average molecular weight $M_w$, of 750. 37.5 grams of triphenyl phosphate, 42.0 grams of p-tert-octylphenol, and 0.2 gram of magnesium chloride. The reaction mixture was then heated to about 190° C. under a vacuum of about 20 millibars, at which time phenol began to distill off. A phenol distillate in the amount of 52 grams was collected over a period of 2 hours during which time the flask contents temperature increased to about 200° C. The resulting mixture was vacuum stripped under 5 millibars for 25 minutes. After cooling to room temperature (about 25° C.), the resulting mixture was diluted with 1 liter of ethyl acetate and cooled with an ice bath. With stirring, 15 milliliters of 30 percent hydrogen peroxide aqueous (water) solution were added at a rate such that the internal temperature was maintained below about 40° C. After the addition, the reaction mixture was stirred for 3.0 hours, then transferred into a separation funnel, and washed with saturated sodium chloride aqueous solution. The organic layer containing the surfactant and solvent was separated, and dried over magnesium sulfate. After the solid was filtered, 25 the solvent in the liquid filtrate was distilled off to yield 157 grams of surfactant (XV). The surfactant composition product was characterized by proton NMR. The chemical shifts in $CDCl_3$ were 0.7 (s), 1.36 (s), 1.70 (s), 3.39 (s), 3.66 (m, PEG backbone), 4.28 (m), 7.10~7.40 (m).

EXAMPLE V
Synthesis of Bisα-methyl Ether ω-methyl 4-tert-octylphenyl Phospate (XVI) Wherein m is About 40:

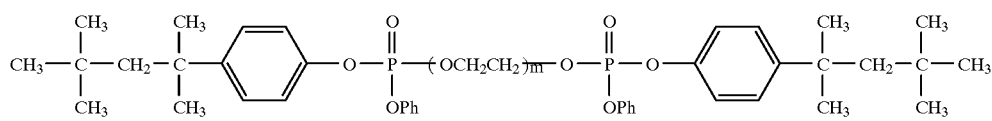 (XVI)

In a 3 liter round bottomed flask equipped with a mechanical stirrer and a fractionating column, a distillation head and a condenser, which is connected to a vacuum line, there were added 150 grams of poly(ethylene glycol) with an average molecular weight of 1,500, 75.0 grams of triphenyl phosphite, 80.0 grams of p-tert-octylphenol, and 0.6 gram of magnesium chloride. The reaction mixture was then heated to about 190° C. under a vacuum of about 20 millibars, at which time phenol began to distill off. A phenol distillate in the amount of 19 grams was collected over a period of 2 hours during which time the reactants temperature increased to about 210° C. The resulting mixture was vacuum stripped under 5.0 millibars for 25 minutes. After cooling to room temperature (about 25° C.), the mixture was diluted with 1.0 liter of ethyl acetate, and treated with 30 grams 30 percent hydrogen peroxide as described in Example I yielding 190 grams of surfactant (XVI). The surfactant composition was characterized by proton NMR. The chemical shifts in $CDCl_3$ were 0.7 (s), 1.37 (s), 1.71 (s), 3.38 (s), 3.65 (m, PEG backbone), 4.38 (m), 7.08~7.41 (m).

Other modifications of the present invention may occur to those skilled in the art subsequent to a review of the present application and these modifications, including equivalents and substantial equivalents thereof, are intended to be included within the scope of the present invention.

What is Claimed is:

1. A process for the preparation of a compound represented by Formulas (I), (II) or (III); or optionally mixtures thereof

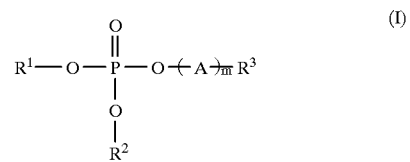 (I)

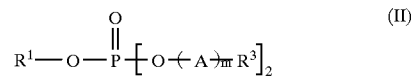 (II)

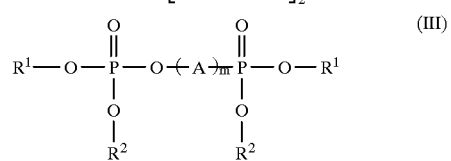 (III)

wherein $R^1$ is a hydrophobic moiety of alkyl or aryl; $R^2$ is selected from the group consisting of alkyl and aryl; $R^3$ is hydrogen or alkyl; A is a hydrophilic polymer chain; and m is the number of repeating segments of the hydrophilic polymer chain A; and which process comprises:

(a) reacting a phosphorus acid ester of the following Formula (IV)

 (IV)

wherein $R'$ is aryl, $R^2$ is alkyl or aryl with a hydrophilic polyoxyalkylene of the following Formulas (VIII), or (IX)

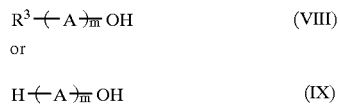

$$R^3\text{---}(A)_{\overline{m}}\text{OH} \quad \text{(VIII)}$$

or $$H\text{---}(A)_{\overline{m}}\text{OH} \quad \text{(IX)}$$

wherein $R^3$ is alkyl with from about 1 to about 6 carbon atoms, and A is a hydrophilic polyoxyalkylene chain, and which reaction results in an intermediate compound Formulas (XI), (XII), or (XIII), wherein component (XI) results from the reaction of phosphorus ester (IV) with polyoxyalkylene (VIII); component (XII) results from the reaction of phosphorus ester (IV) with polyoxyalkylene (VIII), and component (XIII) results from the reaction of phosphorus ester component (IV) with polyoxyalkylene glycol (IX)

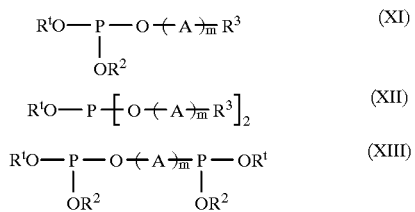

(b) reacting the intermediate compound selected from the group consisting of Formulas (XI) through (XIII), with a hydroxylic compound, $R^1$-OH (X), to yield surfactant precursors comprised of Formulas (V), (VI), and (VII) respectively, wherein component (V) results from the reaction of component (XI) with $R^1$-OH (X); component (VI) results from the reaction of component (XII) with $R^1$-OH (X), and component (VII) results from the reaction of component (XIII) with $R^1$-OH (X)

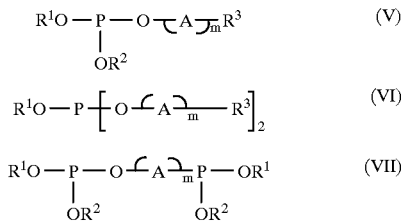

wherein for (b) $R'$ is aryl, $R^1$ is alkyl or aryl, $R^2$ is alkyl or aryl, $R^3$ is hydrogen or alkyl, A is a hydrophilic polymer chain, and m is the number of repeating segments (c) oxidizing said phosphorus ester-linked surfactant precursors (B) selected from the group consisting of Formulas (V), (VI) and (VII), with an oxidizing agent to produce the surfactant composition of Formulas (I), (II) or (III), wherein the surfactant (I) results from the oxidation of component (V), surfactant (II) results from the oxidation of component (VI), and surfactant (III) results from the oxidation of component (VII).

2. A process in accordance with claim 1 wherein there is accomplished a transesterification reaction of (a) and (b), and which reaction is effected by heating at a temperature of about 150° C. to about 250° C. under a reduced pressure of from about 1.0 to about 100 bar, and wherein the byproduct of R'OH is optionally removed.

3. A process in accordance with claim 1 wherein the reactants for the formation of surfactant of Formula (I) comprise from 1 to about 1.2 molar equivalents of a phosphorus ester (IV), about 1.0 molar equivalent of a polyoxyalkylene (VIII), and from about 1.0 to about 1.2 molar equivalents of (X).

4. A process in accordance with claim 1 wherein the reactants for the formation of Formula (II) comprise from 1 to about 1.2 molar equivalent of a phosphorus ester (IV), and about 2.0 molar equivalents of a polyoxyalkylene (VIII).

5. A process in accordance with claim 1 wherein the reactants for the formation of Formula (III) comprise from 2 to about 2.4 molar equivalents of a phosphorus ester (IV), about 1.0 molar equivalent of a polyoxyalkylene (VIII), and from about 2.0 to about 2.4 molar equivalents of an alcoholic compound (X).

6. A process in accordance with claim 1 wherein there is accomplished a transesterification reaction of (a) and (b), and which reaction further includes a catalyst, and which catalyst is selected from the group consisting of metal salts, alkaline metal hydroxides, and alkaline metal alkoxides.

7. A process in accordance with claim 6 wherein said metal catalyst is magnesium chloride.

8. A process in accordance with claim 1 wherein the oxidation (c) is accomplished in an inert solvent at from 0° C. to about 60° C. with an oxidizing agent selected from the group consisting of hydrogen peroxide, ozone, organic hydrogen peroxides, and peracids.

9. A process in accordance with claim 8 wherein said oxidizing agent is hydrogen peroxide or tert-butyl hydrogen peroxide.

10. A process in accordance with claim 8 wherein said inert solvent is ethyl acetate, toluene, or dichloromethane.

11. A process in accordance with claim 1 wherein said $R'$ of the phosphorus ester of Formula (IV) is selected from the group consisting of phenyl, tolyl, fluorophenyl, and chlorophenyl.

12. A process in accordance with claim 1 wherein $R'$ is a phenyl.

13. A process in accordance with claim 1 wherein $R^1$ alkyl contains from about 4 to about 60 carbon atoms, $R^1$ aryl contains from about 6 to about 60 carbon atoms; $R^2$ alkyl contains from about 1 to about 60 carbon atoms, $R^2$ aryl contains from about 6 to about 60 carbon atoms; $R^3$ alkyl contains from 1 to about 6 carbon atoms; and m is a number of from about 2 to about 500.

14. A process in accordance with claim 1 wherein A is a hydrophilic polyoxyalkylene chain derived from the same or different alkylene oxides with from about 2 to about 4 carbon atoms.

15. A process in accordance with claim 1 wherein $R^1$ is an alkylaryl, and wherein alkyl contains from about 4 to about 30 carbon atoms and aryl contains from about 6 to about 10 carbon atoms; $R^2$ is an alkyl containing from 1 to about 30 carbon atoms or an aryl containing from about 6 to about 10 carbon atoms; $R^3$ is hydrogen or alkyl of from 1 to about 3 carbon atoms; and wherein A is a hydrophilic polyoxyalkylene chain with the number of repeating segments m being from about 5 to about 100.

16. A process in accordance with claim 1 wherein A is a poly(ethylene glycol) chain with the number of repeating units m being from about 5 to about 100.

17. A process in accordance with claim 1 wherein $R^1$ is an alkylphenyl group wherein alkyl contains from about 4 to about 30 carbon atoms, $R^2$ is a phenyl, and $R^3$ is a methyl, and wherein A is a poly(ethylene glycol) chain with the number of repeating units m being from about 5 to about 100.

18. A process in accordance with claim 1 wherein said compound resulting is selected from the group consisting of poly(ethylene glycol)-α-methyl ether-ω-p-tert-octyldiphenyl phosphate, poly(ethylene glycol)-α-methyl ether-ω-octyldiphenyl phosphate, poly(ethylene glycol)-αmethyl ether-ω-decyldiphenyl phosphate, poly(ethylene glycol)-α-methyl ether-ω-dodecyldiphenyl phosphate, poly(ethylene glycol)-α-methyl ether-ωhexadecyldiphenyl phosphate, poly(ethylene glycol)-α-methyl ether-ωmethyl p-tert-octylphenyl phosphate, bis -ω-p-tert-octylphenyl phosphate, poly(ethylene glycol)-α,ω-methyl p-tert-octylphenyl phosphate, poly(ethylene glycol) ethyl p-tert-octylphenyl phosphate, poly(ethylene glycol)-α-methyl ether-ω-ethyl p-tert-octylphenyl phosphate, poly(ethylene glycol)-α-methyl ether-ω-p-tert-octylphenyl tolyl phosphate, poly(ethylene oxide-co-propylene oxide)-α-methyl ether-ω-p-tert octyldiphenyl phosphate, and wherein the polymer chain contains from about 5 to about 50 repeating units or segments.

19. A process in accordance with claim 1 wherein $R^t$ is phenyl, $R^1$ is 4-octylphenyl or 4-dodecylphenyl, $R^2$ is a phenyl or methyl, and $R^3$ is a methyl.

20. A process in accordance with claim 1 wherein the hydrophobic compound $R^1$-OH (X) is 4-tert-octylphenol or 4-dodecylphenol.

21. A process in accordance with claim 1 wherein said phosphorus ester is triphenyl phosphite.

22. A process in accordance with claim 1 wherein the oxidizing agent is selected from the group consisting of hydrogen peroxide, ozone, organic hydrogen peroxides and peracids.

23. A process in accordance with claim 1 wherein the oxidizing agent is selected from the group consisting of tert-butyl hydrogen peroxide, cumene peroxide, peracetic acid and performic acid.

24. A process for the preparation of a poly(ethylene glycol)-α-methyl ether-ω-p-tert-octyldiphenyl phosphate comprising the reaction of about 1.0 molar equivalent of poly(ethylene glycol) monomethyl ether with $M_n$, of from about 500 to about 2,000, from about 1.0 to about 1.5 molar equivalents of triphenyl phosphite, from about 1.0 to about 1.5 molar equivalents of 4-tert-octylphenol, and from about 0.01 to about 0.05 molar equivalent of magnesium chloride, with an oxidizing agent and wherein the oxidation optionally includes from about 1.0 to about 1.5 molar equivalents of hydrogen peroxide.

25. A process for the preparation of a component represented by Formulas (I), (II) or (III); or optionally mixtures thereof

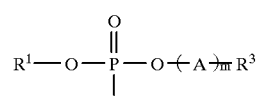 (I)

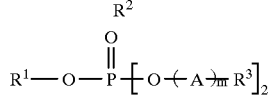 (II)

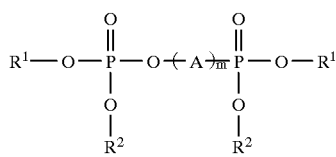 (III)

wherein $R^1$ is a hydrophobic moiety; $R^2$ is a suitable aliphatic or aromatic group; $R^3$ is hydrogen or aliphatic; A is a hydrophilic polymer chain; and m is the number of repeating segments of the hydrophilic polymer chain A; and which process comprises (a) reacting a phosphorus acid ester of the following Formula (IV)

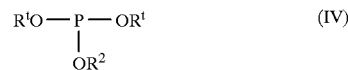 (IV)

wherein $R^t$ is aryl, $R^2$ is a suitable aliphatic or aromatic group with a hydrophilic polyoxyalkylene of the following Formulas (VIII), or (IX)

 (VIII)

or

 (IX)

wherein $R^3$ is alkyl, and A is a hydrophilic polyoxyalkylene chain, and which reaction results in a compound of Formulas (XI), (XII), or (XIII), wherein component (XI) results from the reaction of phosphorus ester (IV) with polyoxyalkylene (VIII); component (XII) results from the reaction of phosphorus ester (IV) with polyoxyalkylene (VIII), and component (XIII) results from the reactions of phosphorus ester component (IV) with polyoxyalkylene glycol (IX)

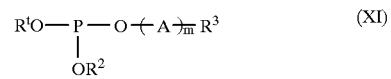 (XI)

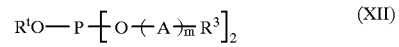 (XII)

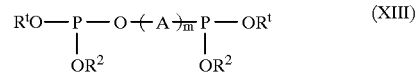 (XIII)

(b) reacting the compound selected from the group consisting of Formulas (XI) through (XIII) with a hydroxylic compound $R^1$-OH (X) to yield compounds of Formulas (V), (VI), and (VII), respectively, wherein component (V) results from the reaction of component (XI) with $R^1$-OH (X); component (VI) results from the reaction of component (XII) with $R^1$-OH (X), and component (VII) results from the reaction of component (XIII) of $R^1$-OH (X)

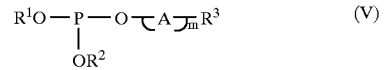 (V)

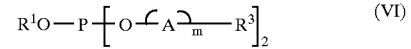 (VI)

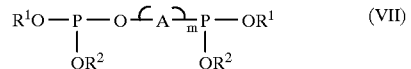 (VII)

(c) oxidizing said phosphorus ester-linked compound (b) selected from the group consisting of Formulas (V), (VI) and (VII), with an oxidizing agent to generate Formulas (I), (II) or (III), wherein (I) results primarily from the oxidation of component (V), (II) results primarily from the oxidation of component (VI), and (III) results primarily from the oxidation of component (VII).

* * * * *